US008063059B2

(12) United States Patent
Hermann

(10) Patent No.: US 8,063,059 B2
(45) Date of Patent: Nov. 22, 2011

(54) USE OF COMPOSITIONS CONTAINING KAPPA-OPIOID RECEPTOR ANTAGONISTS FOR THE TREATMENT OF DISSOCIATIVE DISORDERS

(75) Inventor: Lars Holger Hermann, Schindellegi (CH)

(73) Assignee: Emodys GmbH, Schindellegi (CH)

( * ) Notice: Subject to any disclaimer, the term of this patent is extended or adjusted under 35 U.S.C. 154(b) by 46 days.

(21) Appl. No.: 12/296,125

(22) PCT Filed: Apr. 3, 2007

(86) PCT No.: PCT/EP2007/053248
§ 371 (c)(1),
(2), (4) Date: Jan. 22, 2009

(87) PCT Pub. No.: WO2007/115975
PCT Pub. Date: Oct. 18, 2007

(65) Prior Publication Data
US 2009/0181999 A1   Jul. 16, 2009

(30) Foreign Application Priority Data

Apr. 4, 2006   (DE) .......................... 10 2006 015 733
Apr. 11, 2006  (DE) .......................... 10 2006 016 991

(51) Int. Cl.
*A61K 31/485* (2006.01)
*A61P 25/00* (2006.01)
*C07D 221/22* (2006.01)

(52) U.S. Cl. .......................................... 514/282; 546/39
(58) Field of Classification Search .................. 514/282; 546/39
See application file for complete search history.

(56) References Cited

U.S. PATENT DOCUMENTS

| 5,028,612 | A | 7/1991 | Glover | |
| 5,780,479 | A * | 7/1998 | Kim | 514/282 |
| 6,242,456 | B1 | 6/2001 | Shuster et al. | |
| 2002/0045572 | A1 | 4/2002 | Clemens | |
| 2002/0091075 | A1 | 7/2002 | Carlezon, Jr. | |
| 2007/0231269 | A1 | 10/2007 | Birch et al. | |

FOREIGN PATENT DOCUMENTS

| EP | 0451009 A2 | 9/1991 |
| WO | 0213759 A2 | 2/2002 |
| WO | 0249643 A1 | 6/2002 |
| WO | 03080022 A2 | 10/2003 |
| WO | 2005084654 A2 | 9/2005 |
| WO | 2005117838 A1 | 12/2005 |

OTHER PUBLICATIONS

Simeon, Daphne, "Depersonalisation Disorder; A Contempory Overview", CNS Drugs, Adis Data International, Auckland, NZ, vol. 18 No. 6, 2004, pp. 343-354, XP009085195.
Mague, Stephen D. et al., Antidepressant-Like Effects of k-Opioid Receptor Antagonisgts in the Forced Swim Test in Rats, Journal of Pharmacology and Experimental Therapeutics, vol. 365 No. 1, Apr. 1, 2003, pp. 323-330, XP002437983.
Vadivelu, Nalini et al., "Buprenorphine Pharmacology and Clinical Applications", Seminars in Anethesia, Saunders, CO, New York, NY, vol. 23, No. 4, Dec. 2004, pp. 281-290, XP004727515.
Maremmani, I. et al., "Buprenorphine As a Psychoactive Drug", Italian Journal of Psychopathology, 2006, Italy, vol. 12, No. 3, 2006, pp. 332-341, XP002437984.
Metcalf, Mathew D et al., "Kappa Opioid Antagonists: Past Successes and Future Prospects", AAPS Journal 2005, vol. 7, No. 3, pp. E704-E722, XP002437985.

* cited by examiner

*Primary Examiner* — Jason Sims
*Assistant Examiner* — Zohreh Vakili
(74) *Attorney, Agent, or Firm* — Patent Central LLC; Stephan A. Pendorf

(57) ABSTRACT

The invention relates to the use of a composition comprising kappa opioid receptor antagonists for producing a drug for the treatment of dissociative disorders in humans.

18 Claims, No Drawings

USE OF COMPOSITIONS CONTAINING KAPPA-OPIOID RECEPTOR ANTAGONISTS FOR THE TREATMENT OF DISSOCIATIVE DISORDERS

FIELD OF THE INVENTION

The present invention relates to the use of a composition containing kappa-opioid receptor antagonists or the use of a composition containing kappa-opioid receptor antagonists for the production of a drug in each case for the treatment of dissociative disorders in the human.

The term "dissociative disorders" used within the scope of the present invention more particularly relates to specific personality disorders (F60 of ICD-10), emotionally unstable personality disorders (F60.3 of ICD-10), combined and other personality disorders (F61 of ICD-10) and psychic illnesses in which dissociative symptom complexes (optionally together with other symptom complexes) play a major part.

Dissociative Disorders

The term dissociative disorders is generally understood to mean the partial or complete loss of the normal integration of the memory with respect to the past, identity awareness, the perception of direct sensations and the control of body movements and symptoms in which there is a separation of psychic functions such as the power of recollection, own feelings (e.g. pain, fear, hunger, thirst), the perception of the individual person and/or the environment.

Chronic disorders, particularly paralyses and paraphias, evolve if the start of the dissociative disorder was linked with insoluble problems or interpersonal difficulties. Such disorders used to be classified as different forms of "conversion neurosis or hysteria". They are looked upon as causally psychogenic, closely time related with traumatizing events, insoluble or intolerable conflicts or disturbed relationships.

Adaptation disturbances are triggered by extremely stressing life events giving rise to an acute stress reaction, or through a particular change in life which has led to a persistent unpleasant situation.

Although less severe psychosocial stresses (life events) can trigger and influence the start and manifestation of numerous other disturbances, their etiological significance is not always completely clear. As opposed to this, the disturbances indicated within the scope of the present invention are always a direct consequence of an acute, severe stress or a continuous trauma. The stressing event or the persistent, unpleasant circumstances are primary, decisive causal factors and without their action the disturbance would not have arisen.

The dissociative disorders within the scope of the present invention generally relate to dissociative disorders in the sense of the international classification of diseases (ICD-10), dissociative disorders within the framework of personality disturbances, dissociative disturbances within the framework of abnormal habits and disturbances to the impulse control and within the framework of post traumatic stress disorders. Dissociative disorders are preferably selected from among dissociative disturbances or conversion disturbances, dissociative amnesia, dissociative fugue, dissociative stupor, trance and obsession states, dissociative movement disorders, dissociative convulsions, sensory dissociation and esthesia, not further defined dissociative disturbances and mixed dissociative disturbances relative to the above types. When dissociative states occur in personality disorders they are preferably chosen from specific personality disorders, paranoid personality disturbance, schizoid personality disturbance, dissocial personality disturbance, emotionally unstable personality disturbance, histrionic personality disturbance, anankastic personality disturbance, anxious (avoidance) personality disturbance, dependence personality disturbance and other personality disturbances or not further defined personality disturbances, as well as persistent personality change, which is not a consequence of injury or disease of the brain, persistent personality change following extreme stress, persistent personality change following psychic illness or any other persistent personality changes or not further defined personality changes.

Behavioural disturbances are preferably chosen from among abnormal habits and disturbances to the impulse control such as pathological playing or gaming, pathological fire lighting (pyromania), pathological stealing (kleptomania), trichotillomania and other abnormal habits and disturbances of the impulse control and not further defined abnormal habits and disturbances to the impulse control.

Post Traumatic Stress Disorder

Within the scope of the present invention particular account must be taken of post traumatic stress disorder. This arises as a delayed or protracted reaction to a stressing event or a situation having a duration of varying length, with an extreme threat or catastrophe-like extent, which in almost all cases would give rise to severe despair. Typical features are the repeated reliving of the trauma in obtruding memories (flashbacks), dreams or nightmares occurring against the background of a persistent feeling of lethargy and emotional apathy. There is also an indifference to other humans, apathy relative to the surroundings and gloominess or a feeling of disinterest in the sense of a dissociation experience and avoidance of activities and situations which would bring back memories of the trauma. There is usually a state of vegetative erethism with an increase of vigilance, an excessive feeling of terror and sleep disturbance. Fear and depression are not infrequently associated with the indicated symptoms and features and there are not infrequent thoughts of suicide.

Emotionally Unstable Personality Disorder

Examples of personality disorders which can in part have serious consequences for the person in question are also emotionally unstable personality disorders (also known as the borderline syndrome), as well as other mixed personality disorders.

An emotionally unstable personality disorder is understood to mean a personality disorder with a clear tendency of acting out impulses without taking account of the consequences linked with an unpredictable and moody behaviour. There is a tendency to emotional outbursts and an incapacity to control impulse-based behaviour. There are also highly changing moods and affects, a shattered self-image, widely differing and marked types of trauma-caused dissociations and associated autoaggression.

For the treatment of emotionally unstable personality disorder (borderline syndrome) numerous therapy methods have been evolved, but mostly only with a moderate success.

Problem and Solution

The problem of the present invention is to provide alternative and optionally improved treatment methods for dissociative disorders.

The problem is solved by the use of a composition containing at least one kappa-opioid receptor antagonist or the use of a composition containing at least one kappa-opioid receptor antagonist for the production of a drug, in each case for the treatment of dissociative disorders.

The at least one kappa-opioid receptor antagonist can be in pure form or in the form of a pharmaceutically acceptable salt, ester, ether, tautomer and/or hydrate.

As kappa-opioid receptor antagonists use can be made of compounds or their pharmaceutically acceptable salts, ethers, esters, tautomers and/or hydrates, such as are e.g. described by D. Metcalf and A. Coop in The AAPS Journal 2005; 7 (3), art. 71 (Oct. 27, 2005), pp 704 to 722.

The opioid receptor system comprises three types of heterogeneous, G-protein-coupled opioid receptors, namely μ (mue)-, $\bar{o}$- and κ (kappa) receptors, each of said receptors having selective agonists and antagonists. Antagonists (blockers) have a high affinity for the receptor with the lack or limited intrinsic activity (action). The reaction mechanism of the antagonists on the receptor can be subdivided into competitive and non-competitive antagonism. Competitive means that with an excess of an agonist the antagonist may be clearly displaceable from the receptor. With non-competitive antagonism said displacement reaction is not or is only possible to a limited extent, e.g. by the irreversible binding of the antagonist or by a reaction of the antagonist with a receptor point other than the agonist binding point.

Within the scope of the present invention it is possible to use various kappa-opioid receptor antagonists, e.g. selective kappa-opioid receptor antagonists or those which interact with other receptor centres. The latter have mixed agonist and antagonist proportions, e.g. in the case of the different opioid receptors. For example, buprenorphine (according to the following formula VI) can act both as a kappa-opioid receptor antagonist and as a mue-opioid receptor agonist. Complete agonists, which act non-specifically on all opioid receptors and therefore evolve other modes of action, can be used in additive form in the present invention so as to introduce further advantageous effects into the products produced according to the invention. An example of the last-mentioned class is naloxone.

Selective Kappa-Opioid Receptor Antagonists

It is possible to use selective kappa-opioid receptor antagonists of general formula I:

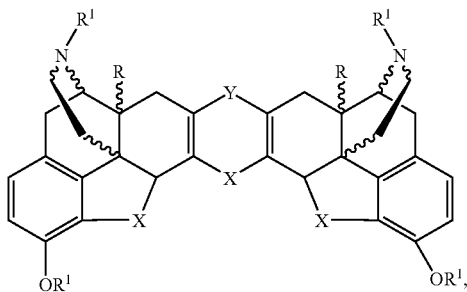

wherein
the radicals R, $R^1$ and X can in each case be the same or different,
X, independently of one another is O, NH, N—$C_{1-6}$-alkyl or S,
Y—$(CHR^1)_m$ with m=0, 1 or 2,
$R^1$H is straight chain or branched $C_{1-12}$-alkyl, straight chain or branched $C_{2-12}$-alkenyl, straight chain or branched $C_{2-12}$-alkinyl, —$(CH_2)_n$—$C_{3-8}$-cycloalkyl, —$(CH_2)_n$—$C_{3-8}$-cycloalkenyl, —$(CH_2)_n$—$C_{3-8}$-heterocycloalkyl, —$(CH_2)_n$—$C_{3-8}$-heterocycloalkenyl, —$(CH_2)_n$—$C_{6-14}$-aryl or —$(CH_2)_n$—$C_{6-14}$-heteroaryl, all the radicals being unsubstituted or substituted with halogen, —OH, —$NO_2$, —$NH_2$, —$NHC_{1-6}$-alkyl, —$N(C_{1-6}$-alkyl$)_2$, —NH(C=NH)$NH_2$ or —O—$C_{1-6}$-alkyl and a methylene group of the above radicals can be replaced by —(C=O)— and n is in each case independently of one another 0, 1, 2, 3, 4, 5 or 6, and
and R is halogen, —OH, —$NO_2$, —$NH_2$, —$NHC_{1-6}$-alkyl, —$N(C_{1-6}$-alkyl$)_2$, —NH(C=NH)$NH_2$, —O—$C_{1-6}$-alkyl or $R^1$,
or pharmaceutically acceptable salts, esters, ethers, tautomers and/or hydrates thereof.

The selective kappa-opioid receptor antagonists covered by the general formula I include e.g. binaltorphimine (BNI) and norbinaltorphimine (norBNI) and derivatives and isomers thereof, e.g. furan or pyran analogs.

It is also possible to use selective kappa-opioid receptor antagonists of general formula II:

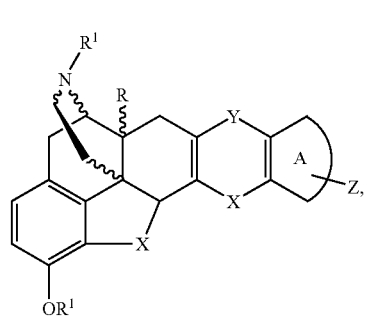

wherein
the radicals R, $R^1$ and X can in each case be the same or different,
R, $R^1$, X and Y are as defined in formula I,
the ring A is a 5-14 member, aliphatic, heteroaliphatic, aromatic or heteroaromatic, mono- or bicyclic ring (preferably a 6-member monocyclic, aromatic or heteroaromatic ring), which can optionally be substituted with Z,
in which Z is halogen, straight chain or branched $C_{1-12}$-alkyl, straight chain or branched $C_{2-12}$-alkenyl, straight chain or branched $C_{2-12}$-alkinyl, —$(CH_2)_n$—$C_{3-8}$-cycloalkyl, —$(CH_2)_n$—$C_{3-8}$-cycloalkenyl, —$(CH_2)_n$—$C_{3-8}$-heterocycloalkyl, —$(CH_2)_n$—$C_{3-8}$-heterocycloalkenyl, —$(CH_2)_n$—$C_{6-14}$-aryl, —$(CH_2)_n$—$C_{6-14}$-heteroaryl, —$(CH_2)_n$—$NH_2$, —$(CH_2)_n$—NH(C=NH)—$C_{1-8}$-alkyl, —$(CH_2)_n$—NH(C=NH)—$NH_2$, —$(CH_2)_n$—NH(C=NH)NH(C=NH)$NH_2$, —$(CH_2)_n$—NH(C=N—CN)$NH_2$, —$(CH_2)_n$—C=O—$C_{1-8}$-alkyl, —$(CH_2)_n$—C=O—$C_{1-6}$-alkyl-NH—C=O—$C_{1-6}$-alkyl-$NH_2$, —$(CH_2)_n$—NH(C=S)$NH_2$, —$(CH_2)_n$—NH(C=NH)S—$C_{1-6}$-alkyl, —$(CH_2)_n$—(C=NH)$NH_2$, —$(CH_2)_n$—NH(C=NH)NH—$C_{1-6}$-alkyl, —$(CH_2)_n$—C=O—NH—$C_{1-8}$-alkyl, —$(CH_2)_n$—C=O—NH-aryl, —$(CH_2)_n$—C=O—NH—$C_{1-6}$-alkylaryl, where all the radicals can be unsubstituted or substituted with halogen, —$NO_2$, —OH, —$NH_2$, —$NHC_{1-6}$-alkyl, —$N(C_{1-6}$-alkyl$)_2$, —NH(C=NH)$NH_2$ or —O—$C_{1-6}$-alkyl, one or more hydrogen atoms can be replaced by $C_{1-6}$-alkyl, aryl or $C_{1-6}$-alkylaryl and a methylene group of the above radicals can be replaced by —(C=O)- and
n in each case independently of one another is 0, 1, 2, 3, 4, 5 or 6,
or pharmaceutically acceptable salts, esters, ethers, tautomers and/or hydrates thereof.

The kappa-opioid receptor antagonists covered by general formula II e.g. include indole morphinans and amidines, such as guanidine naltrindole (GNTI) and derivatives and isomers thereof.

It is also possible to use selective kappa-opioid receptor antagonists of general formula III:

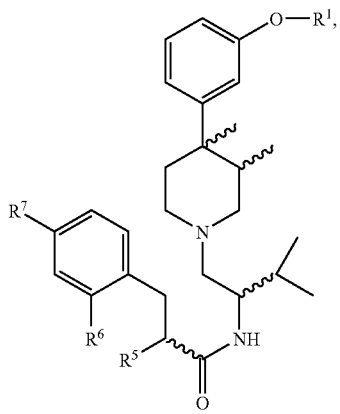

III wherein
- $R^1$ has the meaning defined under general formula I (preferably H and $C_{1-3}$-alkyl),
- $R^5$ and $R^6$ are preferably H, —OH, —SH, —NH or —N—$C_{1-6}$-alkyl and $R^5$ and $R^6$ optionally together can form a carbocyclic or heterocyclic ring with 5 to 7 members, particularly 6 members and
- $R^7$ is H, —OH or —O—$C_{1-6}$-alkyl, particularly —OH, or pharmaceutically acceptable salts, esters, ethers, tautomers and/or hydrates thereof.

Compounds covered by general formula III are inter alia so-called non-epoxymorphinans, such as JDTic, trans-(3R, 4R)-dimethyl-4-(3-hydroxyphenyl)-piperidine, derivatives and isomers thereof.

It is also possible to use selective kappa-opioid receptor antagonists of general structural formula IV:

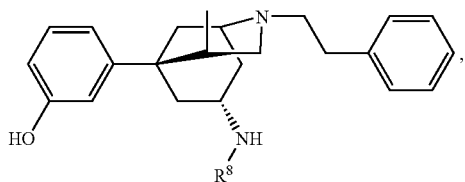

IV wherein
- $R^8$ is H, —(C=O)(CH$_2$)$_n$ piperidine, —(C=O)(CH$_2$)$_n$N (C$_{1-6}$-alkyl)$_2$ or —(C=O)(CH$_2$)$_n$N(C=NH)NH$_2$,
- n is as defined in formula I and
- optionally one or more hydrogen atoms can be replaced by substituted or unsubstituted $R^1$ (as defined in formula I) and a methylene group of the above radicals can be replaced by —(C=O)—, or pharmaceutically acceptable salts, esters, ethers, tautomers and/or hydrates thereof. Preferably n is 2 or 3 and $C_{1-6}$-alkyl is methyl.

It is also possible to use selective kappa-opioid receptor antagonists of general formula V:

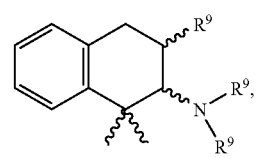

V wherein
- the radicals $R^9$ can be the same or different and can be $R^1$ (as defined in formula I) or a cinnamate are preferably $C_{1-3}$-alkyl,
- a methylene group of the above radicals can be replaced by —(C=O)— and two of the $R^9$ radicals can optionally form a carbocyclic or heterocyclic aliphatic or aromatic ring, or pharmaceutically acceptable salts, esters, ethers, tautomers and/or hydrates thereof.

Further possible selective kappa-opioid receptor antagonists, which can be used within the scope of the present invention are competitive kappa-opioid receptor antagonists, such as the prior art compounds Mr 2266, WIN 44,441 (quadazocine) or triethylene glycol naltrexamine (TENA) of the following formulas:

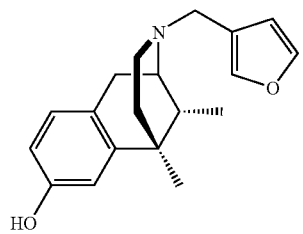

Mr 2266

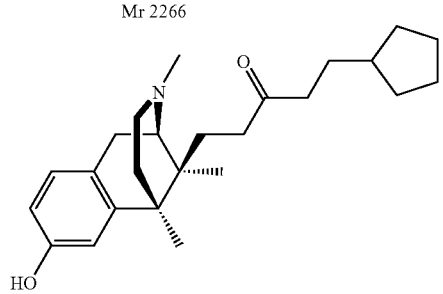

WIN 44,441-3

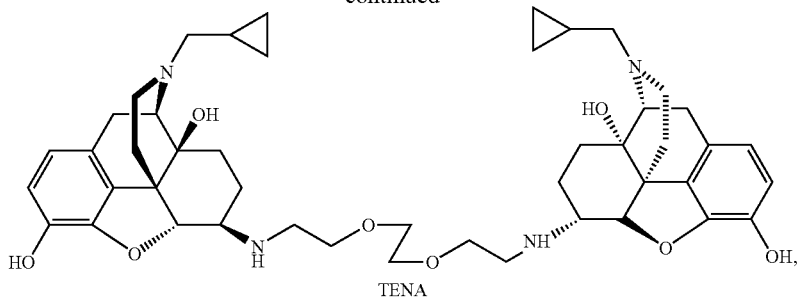

TENA wherein
optionally one or more hydrogen atoms can be replaced by substituted or unsubstituted $R^1$ (as defined in formula I) or a cinnamate and a methylene group of the above radicals can be replaced by —(C=O)— and
wherein O, as desired, can be replaced by S, NH or N—$C_{1-6}$-alkyl,
or pharmaceutically acceptable salts, esters, ethers, tautomers and/or hydrates thereof. Preferably $R^1$ is $C_{1-3}$-alkyl.

Kappa-Opioid Receptor Antagonists, Buprenorphine and its Derivatives

It is also possible to use kappa-opioid receptor antagonists of general formula VI:

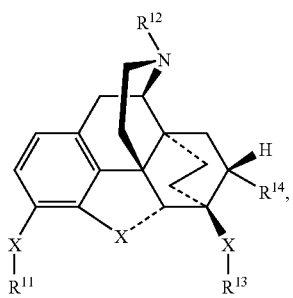

VI wherein
X, independently of one another is O, NH, N—$C_{1-6}$-alkyl or S,
$R^{11}$, $R^{12}$, $R^{13}$ and $R^{14}$, in each case independently of one another, are H, straight chain or branched $C_{1-12}$-alkyl, straight chain or branched $C_{2-12}$-alkenyl, straight chain or branched $C_{2-12}$-alkinyl, —(CH$_2$)$_n$—$C_{3-8}$-cycloalkyl, —(CH$_2$)$_n$—$C_{3-8}$-cycloalkenyl, —(CH$_2$)$_n$—$C_{3-8}$-heterocycloalkyl, —(CH$_2$)$_n$—$C_{3-8}$-heterocycloalkenyl, —(CH$_2$)$_n$—$C_{6-14}$-aryl or —(CH$_2$)$_n$—$C_{6-14}$-heteroaryl, all the radicals can be unsubstituted or substituted with halogen, —OH, —NO$_2$, —NH$_2$, —NHC$_{1-6}$-aryl, —N(C$_{1-6}$-alkyl)$_2$, —NH(C=NH)NH$_2$ or —O—C$_{1-6}$-alkyl and a methylene group of the above radicals can be replaced by —(C=O) and
n, in each case independently of one another is 0, 1, 2, 3, 4, 5 or 6,
or pharmaceutically acceptable salts, esters, ethers, tautomers and/or hydrates thereof.

Preference is given to compounds of general formula VI, wherein
X is O,
$R^{11}$ is H or straight chain $C_{1-6}$-alkyl,
$R^{12}$ is —(CH$_2$)$_n$—$C_{3-4}$-cycloalkyl with n=1 or 2,
$R^{13}$ is H or straight chain $C_{1-6}$-alkyl and
$R^{14}$ is branched $C_{5-8}$-alkyl, which is optionally substituted by —OH,
and pharmaceutically acceptable salts, esters, ethers, tautomers and/or hydrates thereof.

When the compound of general formula VI has the following structure particular preference is given to (2-(N-cyclopropylmethyl-4,5alpha-epoxy-3-hydroxy-6-methoxy-6,14-endoethanomorphinan-7alpha-yl)-3,3-dimethyl-2-butanol (buprenorphin)):

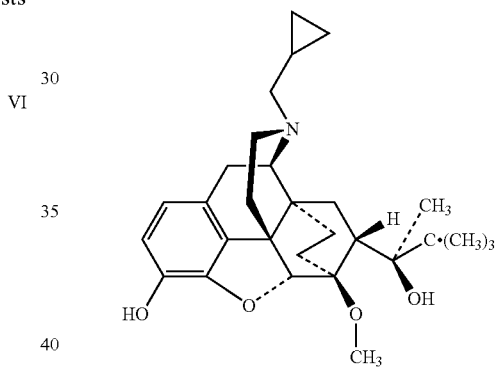

or pharmaceutically acceptable salts, esters, ethers and/or hydrates thereof.

Pharmaceutically acceptable salts for all the compounds referred to within the scope of the invention are preferably chosen from chloride, bromide, iodide, sulphate, phosphate, tartrate, acetate and mucate. The hydrates are preferably selected from mono-, di-, tri-, tetra- and pentahydrate. Preferred esters are carboxylates with $C_{1-6}$-alkyl, acyl, benzyl, benzoate, etc.

When using the aforementioned compounds as drugs, pharmaceutically acceptable carriers as well as adjuvants and additives are optionally admixed.

Pharmaceutically acceptable carriers as well as adjuvants and additives are e.g. a solid, a liquid or a gas. Examples for solid carriers are inter alia lactose, kaolin, saccharose, talc, gelatin, agar, pectin, gum arabic, magnesium stearate and stearic acid. Examples for liquid carriers are molasses, peanut oil, olive oil and water. Examples of gaseous carriers are inter alia carbon dioxide and nitrogen. Examples of adjuvants and additives are diluents, buffers, granulating agents, lubricants, disintegrating agents, binders, surfactants, thickeners, as well as dyes and pigments, preservatives (including antioxidants), flavouring and aromatizing substances.

The compounds of general formulas I to VI, or their pharmaceutically acceptable salts, esters, ethers and/or hydrates are preferably used in a quantity of 1 to 1000 mg, with particular preference 10 to 600 mg and more especially 50 to 500 mg, in each case per administration form, corresponding to 0.01 to 13 mg, preferably 0.1 to 8 mg and more specifically 0.6 to 7 mg per kg of body weight. Administration can take place in the form of powders, tablets, solutions, suppositories or plasters, in each case with a delayed or undelayed release. Other administration forms are conceivable, which permit oral, intravenous, buccal, transdermal, subcutaneous, rectal, inhalative, nasal or sublingual administration. In the case of inhalative administration it may be necessary to admix further (carrier) substances (aerosols, atomizing aids). In the case of nasal administration a supplied powder is e.g. heated and the resulting fumes are breathed in.

In another embodiment of the present invention a compound of formula VI and optionally one or more selective kappa-opioid receptor antagonists of formulas I to V or in each case pharmaceutically acceptable salts, esters, ethers, tautomers, and/or hydrates thereof can be used together with at least one opioid receptor antagonist.

Preferred opioid receptor antagonists are characterized by a limited oral bioavailability, preferably lower than 5%. In the case of oral administration, such substances are subject to a marked first pass metabolism and are therefore rapidly degraded. The antagonists usable within the scope of the present invention have a bioavailability of less than 5%, preferably less than 3% and more specifically less than 1%. Bioavailability here means the proportion in percent or percent by weight of the active ingredient which appears unchanged in the blood when the inventive mixture is orally administered. (The bioavailability of an intravenously injected drug is by definition 100%. For more comprehensive definition reference is made to Rainer K. Liedtke, W"rterbuch der Klinischen Pharmakologie, Gustav Fischer Verlag, Stuttgart, N.Y., 1980. Bioavailability is also defined in WHO annex 9, 1996).

A particularly preferred opioid receptor antagonist is naloxone, which has the following structure:

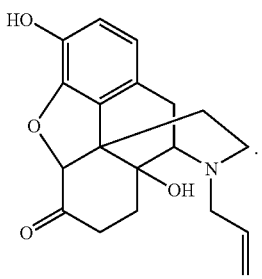

Opioid receptor antagonists, particularly naloxone, can be administered according to the invention in all conventional administration forms. Preference is given to physiologically acceptable, water-soluble salts such as hydrochloride or hydrochloride dihydrate. The opioid receptor antagonist can be present in the inventive product either in retarded or non-retarded form, preference being given to the latter.

Preferred combinations or individual substances conceivable according to the present invention are defined hereinafter ("//" symbolizes a combination). The following meanings are used for A, B and C:

A=selective kappa-opioid receptor antagonists or pharmaceutically acceptable salts, esters, ethers, tautomers and/or hydrates thereof, particularly of formulas I to V;

B=buprenorphine and/or its derivatives or in each case pharmaceutically acceptable salts, esters, ethers, tautomers and/or hydrates thereof, particularly of formula VI;

C=opioid receptor antagonist (preferably naloxone) or pharmaceutically acceptable salts, esters, ethers, tautomers and/or hydrates thereof;

A;
B;
A//B;
A//C;
B//C;
A//B//C.

Within the scope of a particularly preferred embodiment of the present invention use is made of a composition comprising buprenorphine, at least one opioid receptor antagonist and optionally at least one selective kappa-opioid receptor antagonist.

The compounds of general formulas I to VI are produced according to prior art methods. For the production of compounds of general formula VI and in particular buprenorphine reference is made to The Merck Index, 13th edition, 2001, p 252 and the literature references cited therein. Buprenorphine derivatives can also be produced on the basis of buprenorphine using conventional methods. For the production of the compounds of general formulas I to V particular reference is made to "The AAPS Journal 2005; 7 (3), art. 71 (Oct. 27, 2005), pp 704 to 722" and the literature references cited therein.

The production of the inventive drugs in the form of powders, tablets, solutions, suppositories or plasters, in each case with a retarded or non-retarded release takes place in accordance with prior art methods, e.g. by mixing the components, optionally adding carriers as well as adjuvants and additives, followed by further mixing, optionally dissolving or dispersing the components or compressing the components to form a tablet.

Buprenorphine, kappa-opioid receptor antagonists and mixtures of buprenorphine with naloxone and/or kappa-opioid receptor antagonists are particularly appropriate for self-destructive behavioural patterns with parasuicidal actions, self-injuries and suicide attempts.

The present invention is further illustrated by the following production examples and medical application examples, but without being limited thereto.

PRODUCTION EXAMPLES

In the following production examples in each case the indicated pharmaceutically active constituents are mixed with the following adjuvants and compressed to form a retard film tablet: lactose monohydrate, 30% polyacrylate dispersion, methacrylic acid-ethacrylate copolymer (1:1), ammonium-methacrylate copolymer type B, Hypromellose 4000, magnesium stearate, Macrogel 6000, talc, Hypromellose S, titanium dioxide, red oxide E 172.

Production Example 1

200 mg of buprenorphine.

Production Example 2

200 mg of buprenorphine and 100 mg of binaltorphimine (BNI).

Production Example 3

12 or 16 mg buprenorphine.

Production Example 4

12 mg of buprenorphine and 2 mg of naloxone.

Medical Application Examples

In medical application examples 1 to 2 buprenorphine is used alone or in conjunction with a kappa-opioid receptor antagonist or in conjunction with an opioid receptor antagonist, specially with a limitedly bioavailable opioid receptor antagonist for human patients diagnosed with a post traumatic stress disorder or dissociative disorders.

In medical application examples 3 and 4 buprenorphine, alone or in conjunction with a kappa-opioid receptor antagonist, is used for patients diagnosed with emotionally unstable personality disorder as a possibility for treating the personality disorder and reducing the associated social, somatic and psychiatric consequences.

Medical Application Example 1

Buprenorphine in the form of a tablet with an active ingredient content of 12 mg was administered sublingually to a patient diagnosed with post traumatic stress disorders with the corresponding psychiatric symptoms. On increasing the daily dosage to 16 mg of buprenorphine the occurrence of flashback situations decrease significantly, so that the patient could be transferred from hospital to outpatient treatment. Even one year following the start of treatment with buprenorphine there was still a significant improvement to the flashback symptoms and the daily life intrusions on the part of the patient and the patient indicated a clear subjective improvement to lethargy and emotional swings, as well as intrusive dissociation sensations.

Medical Application Example 2

Buprenorphine was administered to a patient in the form of a mucoadhesive sachet with a buprenorphine proportion of 12 mg and a naloxone proportion of 2 mg for the treatment of dissociative disorders. The central points of the psychiatric symptoms of the patient were disturbances in identity awareness, the perception of direct sensations and the control of body movements. Within one week of administering the buprenorphine/naloxone mixture in the form of a sublingual tablet, there was a reduction in identity disturbance and an improvement to the control of body movements. Improvements stabilized after about 4 weeks and was considered both by the patient and therapist as a positive result with clear symptom reductions.

Medical Application Example 3

Buprenorphine was administered as a mucoadhesive sachet with an active ingredient content of 12 mg to a patient diagnosed with emotionally unstable personality disorder. A complete remission of the self-injuring behaviour was observed. Following a daily ingestion of 12 mg improvements stabilized and even after one year was stable with regards to the complete lack of self-injuries. In two other patients there was a significant reduction to the frequency of self-cutting as the central feature of the borderline disease.

Medical Application Example 4

Buprenorphine was administered to a patient diagnosed with emotionally unstable personality disorder in the form of a sublingual tablet with an active ingredient content of 12 mg and a naloxone proportion of 3 mg. There was a clear reduction to the self-injuring behaviour of the patient over a two year period. Over and beyond the clinical action, there was a significant improvement to the psychiatric evaluation scales: symptom checklist 90 (SCL-90-R), clinical global impression scale (CGI) for severity of illness (global improvement and efficacy not rated), dissociation evaluation (DES), structured clinical interview for dissociative disorders (SKID). The investigation scale level remains stable throughout the investigation period.

The invention claimed is:

1. A method for the treatment of emotionally unstable borderline personality disorders, as defined in F60.3 of the International Classification of Diseases (ICD) 10, in the human, said method comprising administering to an individual afflicted with an emotionally unstable personality disorder an amount of a composition effective to reduce or eliminate at least one symptom of said emotionally unstable personality disorder, said composition comprising a kappa-opioid receptor antagonist having the following formula:

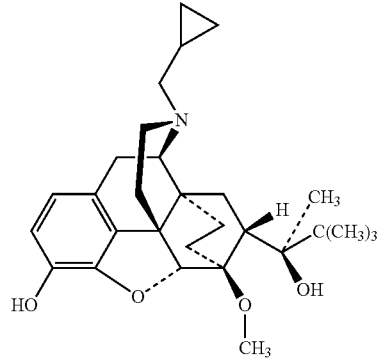

or pharmaceutically acceptable salts, esters thereof selected from carboxylate with $C_{1-6}$ alkyl, acyl, benzyl or benzoate, and/or hydrates thereof.

2. The method according to claim 1, wherein the composition also comprises a further antagonist, said further antagonist being
   (a) a kappa-opioid receptor antagonist; or
   (b) an antagonist of the mu-, delta-, or kappa-opioid receptor.

3. The method according to claim 2, wherein the antagonist of the mu-, delta-, or kappa-opioid receptor is naloxone.

4. The method according to claim 1, the effective amount of the composition is administered daily.

5. The method according to claim 1, wherein the kappa-opioid receptor antagonist is used in a dosage amount of 0.01 to 13 mg per kg of patient body weight.

6. The method according to claim 1, wherein the kappa-opioid receptor antagonist is used in a dosage amount of 0.1 to 8 mg per kg of patient body weight.

7. The method according to claim 4, wherein the kappa-opioid receptor antagonist is used in a dosage amount of 0.6 to 7 mg per kg of patient body weight.

8. The method according to claim 4, wherein the kappa-opioid receptor antagonist is used in a quantity of 1 to 1000 mg.

9. The method according to claim 4, wherein the kappa-opioid receptor antagonist is used in a quantity of 10 to 600 mg.

10. The method according to claim 4, wherein the kappa-opioid receptor antagonist is used in a quantity of 50 to 500 mg.

11. A method for the treatment of emotionally unstable borderline personality disorders, as defined in F60.3 of the International Classification of Diseases (ICD) 10, in the human, said method comprising the steps of:
(a) diagnosing a person as being afflicted with an emotionally unstable borderline personality disorder, as defined in F.60.3 of ICD 10;
(b) determining the amount to be administered of a composition effective to reduce or eliminate at least one symptom of said emotionally unstable borderline personality disorder, said composition comprising a kappa-opioid receptor antagonist having the following formula:

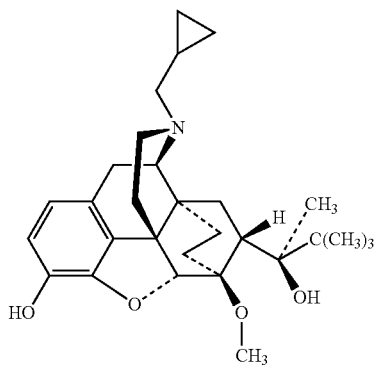

or pharmaceutically acceptable salts, esters thereof selected from carboxylate with C1-6 alkyl, acyl, benzyl or benzoate, and/or hydrates thereof.; wherein said composition is used in a dosage amount of 0.01 to 13 mg per kg of said person's body weight; and
(c) administering to the person the amount of said composition effective to reduce or eliminate at least one symptom of the diagnosed emotionally unstable borderline personality disorder.

12. The method of claim 11, wherein the composition also comprises an opioid receptor antagonist of less than 5% bioavailability.

13. The method of claim 12, wherein the opioid receptor antagonist of limited bioavailability is naloxone.

14. The method of claim 11, wherein the effective amount of the composition is administered daily.

15. The method of claim 11, wherein the administration of the dosage amount is in the form selected from the group consisting of a powder, tablet, solution, suppository, or plaster.

16. The method of claim 11, wherein the administration of the dosage amount is in the form of a type selected from the group consisting of oral, intravenous, buccal, transdermal, subcutaneous, rectal, inhalative, nasal, or sublingual.

17. The method of claim 11, wherein the administration of the dosage amount is in a delayed release form.

18. The method of claim 11, wherein the administration of the dosage amount is in an undelayed release form.

* * * * *